United States Patent [19]

Dahlberg

[11] Patent Number: 5,769,874
[45] Date of Patent: Jun. 23, 1998

[54] ACTIVE MEDICAL IMPLANT WITH A HERMETICALLY SEALED CAPSULE

[75] Inventor: Kenneth Dahlberg, Stockholm, Sweden

[73] Assignee: Pacesetter AB, Solna, Sweden

[21] Appl. No.: 823,361

[22] Filed: Mar. 24, 1997

[30] Foreign Application Priority Data

Mar. 26, 1996 [SE] Sweden ................................. 9601154

[51] Int. Cl.⁶ .................................................. A61N 1/375
[52] U.S. Cl. ............................................................ 607/36
[58] Field of Search ........................................... 607/36, 9

[56] References Cited

U.S. PATENT DOCUMENTS

| | | |
|---|---|---|
| 3,971,388 | 7/1976 | Cowdery . |
| 4,010,759 | 3/1977 | Boer . |
| 4,127,134 | 11/1978 | Ushakoff . |
| 5,131,388 | 7/1992 | Pless et al. . |
| 5,144,946 | 9/1992 | Weinburg et al. . |

FOREIGN PATENT DOCUMENTS 2 055 296  3/1981  United Kingdom .

*Primary Examiner*—Scott M. Getzow
*Attorney, Agent, or Firm*—Hill & Simpson

[57] ABSTRACT

An active medical implant has a hermetically sealable capsule formed by a first part and a second capsule-closing part, whereby the capsule is arranged to hold a battery unit and an electronics unit, conductors for electrically connecting the battery to the electronics unit and contacts with associated conductors arranged on the exterior of the capsule for connection to electrodes. The first part and the second part are made of an essentially biocompatible material, and a partition wall is arranged to form a first essentially closed space in the first part for the battery unit, and an electrically insulating layer, impermeable to battery chemicals, is arranged on the surfaces of the biocompatible material facing the first closed space. An additional space is formed for the electronics between the capsule-closing part and the partition wall.

10 Claims, 1 Drawing Sheet

ACTIVE MEDICAL IMPLANT WITH A HERMETICALLY SEALED CAPSULE

BACKGROUND OF THE INVENTION

1. Field of the Invention

The present invention is directed to an active medical implant, e.g. a pacemaker or defibrillator, containing an electronics unit and an encapsulated battery unit.

As used herein "battery unit" means essentially all parts of the battery, excluding the casing.

2. Description of the Prior Art

The aforementioned devices are intended for use as implants for administering medical therapy. The devices can encompass pulse-generating and, possibly, sensing circuits in addition to batteries. These types of devices are known in the art and are used with good results.

There has always been some concern about the effect that moisture surrounding the implanted device could have on the device's enclosure, since the device inside the enclosure must be able to operate continuously for a number of years, impervious to surrounding human tissue, for reliable functioning. This is conventionally achieved by encapsulating the device in a hermetically sealed enclosure, as set forth in e.g., U.S. Pat. No. 4,127,134, to prevent damage caused pressure resulting from the emission of gas by the battery during operation.

The aforementioned devices must also be protected from damage inflicted by their electrical components. These components are essentially inert, but batteries, capacitors etc. constitute potential risks if they are not carefully encapsulated.

U.S. Pat. No. 4,010,759 describes an insulated, corrosion-resistant pacemaker. The electronic components, including e.g., a pulse generator, in this pacemaker are enclosed in a titanium capsule which has an essentially continuous insulating layer of $Ta_2O_5$, serving as an anode, on its exterior. The layer is provided to prevent leakage currents between a tantalum pin on the capsule and the titanium capsule. The battery is arranged outside the titanium capsule, and the entire device is enclosed in a capsule made of a resin-like material. The patent states that this design is intended to keep the battery from damaging the electronics.

Insulating the exterior of the case is also known from e.g., U.S. Pat. No. 3,971,388.

U.S. Pat. No. 5,144,946 describes e.g. a pacemaker in which a battery and an integral connecting unit are arranged in one part of a two-part case. This known unit contains electronic components and conductors for interconnecting the battery and the electronic circuits, plus terminals for transmitting signals from the pacemaker to the patient. In one embodiment, the integral connecting unit is enclosed in a capsule made of e.g. silicone rubber, i.e. electrical components are insulated from the battery to protect components from any damage caused by the battery.

One example of the encapsulation of non-inert components, a capacitor in this instance, in the devices according to the above-type is described in U.S. Pat. No. 5,131,388. This document also describes the importance of adapting the size of devices intended for use as implants. The document stipulates the use of a material with good corrosion resistance, such as stainless steel or titanium, for encapsulating the capacitor. Encapsulation of a conventional, aluminum electrolytic capacitor, however, is involved in this instance.

Another problem to be considered with devices of this kind is the need to arrange a large number of components during assembly in a manner which saves space and is satisfactory from the safety point of view.

Conventionally, it has proved necessary with devices of the above kind, which utilize lithium-iodine batteries, to encapsulate the battery because battery iodine could attack the electronics or external enclosure. Titanium is not suitable for this enclosure, however, because titanium and even the titanium oxide which forms on it are attacked by iodine. This means that the battery must be encapsulated and kept separated from the external enclosure.

In order to protect devices of the above kind from body fluids and to achieve a device which is largely biocompatible, titanium is advantageously used for the external enclosure, since it has proved to be the most biocompatible material.

Battery systems are now available which have proved to be far more compatible with the titanium enclosure. In addition to lithium-iodine batteries there are e.g. batteries containing substances less corrosive than iodine. For example, a known battery system contains lithium-carbon monofluoride, $Li/CF_x$, in which x is about 1.1. Cells in these systems usually contain a cathode made of a mixture of fluorinated carbon/carbon black plus a binder and an electrolyte, essentially a lithium salt dissolved in an aprotic organic solvent. This system is not damaging to a titanium enclosure in the same way as the lithium-iodine system,

SUMMARY OF THE INVENTION

An object of the present invention is to provide an implant device of the aforementioned kind which is reliable, i.e. which protects components and which is adapted to the environment in which it is to be placed and to the chemicals in the battery unit.

An additional object is to achieve a device which is easy to assemble and seal.

An additional object is to achieve a device of the aforementioned kind with small dimensions.

The above object is achieved in accordance with the principles of the present invention in an active medical implant having a hermetically sealable capsule formed by a first bowl-shaped part and a second capsule-closing part, the first part and the second part being made of biocompatible material, and a partition wall being disposed to form a first substantially closed space in said first part for the battery unit, the partition wall and the first part forming the casing for the battery unit, with the casing being an integral part of the capsule. An electrically insulating layer, impermeable to battery chemicals, is disposed on the surfaces of the biocompatible material facing the first closed space. A second closed space is formed for electronics components between the capsule-closing part and the partition wall.

One advantage achieved with the device according to the invention is that the device's external enclosure is electrically neutral, i.e. it will not affect adjacent tissue, a characteristic which can be desirable. Instead, all electrical activity by the implant is conveyed through implanted electrodes.

An additional advantage is that the implant does not require any particular battery system, so other systems, such as lithium-SVO (silver vanadium oxide) or equivalent systems, can be used with the device according to the invention. It should be noted that connection to the electronics is independent of the battery's construction, since connection between the electronics unit and the battery is via two poles of equivalent design.

DESCRIPTION OF THE PREFERRED EMBODIMENTS

Figure 1:
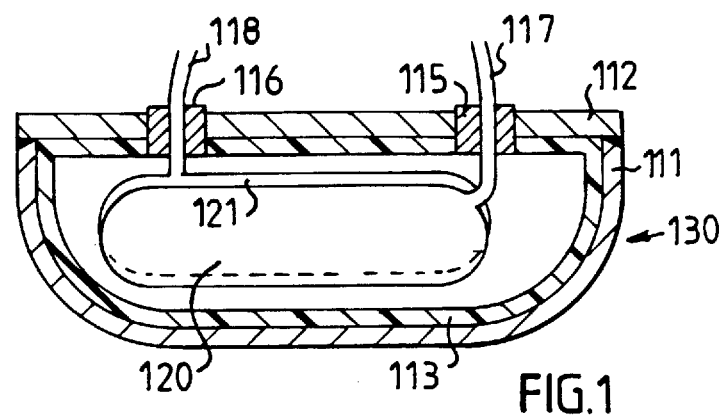
FIG. 1 shows a schematic cross-section of a bipolar embodiment of the encapsulated battery unit according to the invention.

The encapsulated battery unit shown in FIG. 1 is formed by two parts, i.e., a first bowl-shaped part 111 and a second part 112 devised to close the capsule. In this embodiment, the first part 111 and the second part 112 are made of titanium which is, according to the above, a surface material suitable for contact with body tissues. The surface facing the interior of the capsule is given an electrically insulating coating 113, essentially impermeable to battery chemicals such as lithium carbon monofluoride $Li/CF_x$, which encloses the battery unit and electrically separates the titanium surface from battery chemicals. The material layer thus serves as a barrier between e.g. the lithium anode and the titanium surface. The material layer can consist of e.g. polyethylene, halar® (thermoplastic fluoropolymer) film, fluorethene plastic, glass or cermet. The ability to serve as an electrical insulator and impermeability to battery chemicals are the materials most important characteristics.

The second part 112 is welded to the first part ill, so that a sealed space 130 is formed for the battery unit. Hermetically sealed feedthroughs 115 and 116 are arranged through the second part 112 for the battery's respective poles 117 and 118.

In the embodiment shown in the FIG. 1, a lithium anode 120 and a cathode 121, whose active material consists of $CF_x$, are arranged in the sealed space 130. The sealed space 130 also holds an electrolyte consisting mainly of a lithium salt dissolved in an aprotic solvent.

When the second part 112, hereinafter referred in regard to FIG. 2 to as a partition wall 212, is arranged in the first bowl-shaped part ill so it divides a space in the bottom of the bowl-shaped part 111, it becomes possible in a second embodiment of the invention to combine the battery unit with an electronics unit in the same enclosure, i.e. in the titanium enclosure, without any additional encapsulation of the battery unit and/or electronics unit, as noted in the description of FIG. 2.

Figure 2:
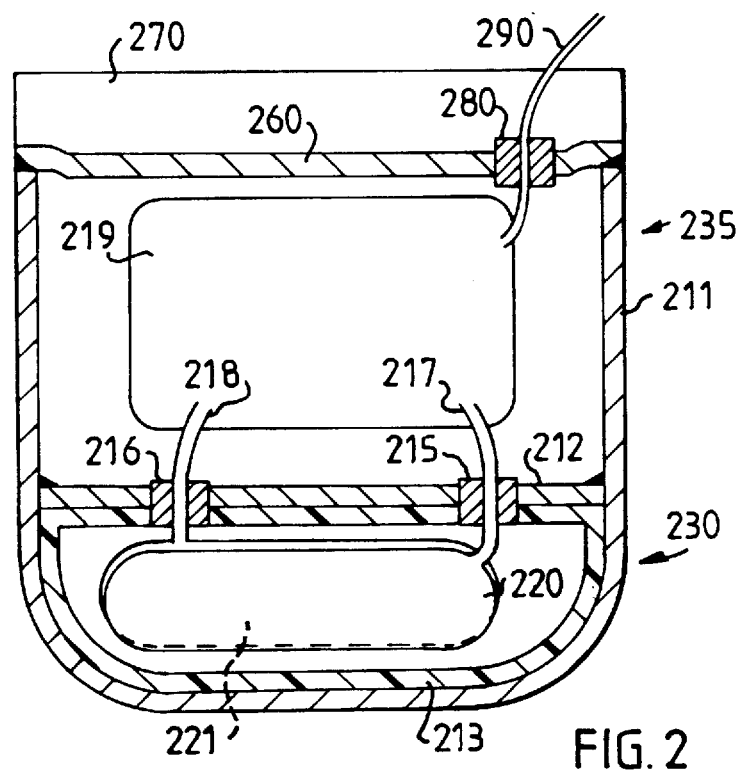
FIG. 2 shows a schematic cross-section of an active implant containing the battery unit according to the invention.

FIG. 2 thus shows an active implant, according to the invention, which has a capsule made of two parts, i.e. a first bowl-shaped part 211 and a second part 260 arranged to close the capsule. And end piece 270 is arranged on the closing second part 260. The first part 211 and the second part 260 are made of titanium, a surface material suitable for contact with body tissues. A partition wall 212 is arranged in the first part 211, essentially parallel to the bottom of the part 211 and divides the part into a space 230 for a battery and a space 235 for an electronics unit 219. The partition wall 212 is preferably made of titanium but could alternatively be made of some other material which is capable of separating the battery space, and the battery enclosed therein, from the electronics unit 219 (not described here) constituting the pacemaker and/or defibrillator, i.e. the active implant, placed in the capsule's second space 235.

The part of the capsule facing the battery space 230 and the surface of the partition wall 212 facing the battery space 230 is provided with an electrically insulating layer which electrically isolates the battery unit from the titanium surface and electrically insulates the surface from the battery unit while simultaneously serving as a coating 213 which is essentially impermeable to battery chemicals, such as lithium-carbon monofluoride $Li/CF_x$. The layer of material therefore constitutes a barrier between e.g., the lithium anode and the titanium surface or between battery fluid and the titanium surface. The layer can consist of e.g. polyethylene, halar® film, fluorethene plastic, glass or cermet. The most important characteristics of this material are that it must be an electrical insulator and impermeable to battery chemicals.

The partition wall 212 is sealingly arranged, e.g. welded to the interior of the first part 211 in such a way that a sealed space is created for the battery unit. Hermetically sealed feedthroughs 215 and 216 are arranged through the partition wall 212 for the battery's respective poles 217 and 218. A feedthrough 280 is arranged in the closing part 260 next to the end block 270 for conductors leading to contacts for connection to electrodes.

In the embodiment shown, a lithium anode 220 and a cathode 221, whose active material consists of $CF_x$ are arranged in the sealed space. An electrolyte, essentially consisting of a lithium salt in an aprotic solvent, is also present.

The above-described embodiments show that a thinner capsule can be achieved for the active implant, since the battery unit, with the implant's enclosure, is an integral unit, and no space is required for an enclosure for a conventional battery/power source. The implant will also contain fewer parts, and reducing the other dimensions of the implant will be possible, since the battery casing is an integral part of the capsule/pacemaker enclosure.

The casing is made of titanium in the described embodiments. Replacing it with some other biocompatible material, such as stainless steel, preferably for the exterior of the enclosure, a cermet, a biocompatible plastic or e.g. perylene or teflon® (tetrafluoroethylene) etc., is also conceivable.

Since the device according to the invention contains fewer parts, production costs will also be reduced.

Although modifications and changes may be suggested by those skilled in the art, it is the intention of the inventor to embody within the patent warranted hereon all changes and modifications as reasonably and properly come within the scope of his contribution to the art.

I claim as my invention:

1. In an active medical implant containing a battery unit and an electronics unit, the improvement of a hermetically sealable capsule comprising:

a first part having a receptacle therein and an open top, and a second part closing said open top, said first part and said second part consisting of biocompatible material;

a partition wall disposed in said first part and forming a substantially closed space in said first part in which said battery unit is disposed, said partition wall and a portion of said first part surrounding said battery unit comprising a hermetically sealed casing for said battery unit as an integral part of said first part;

said hermetically sealed casing having surfaces facing said battery unit with an electrically insulating layer, impermeable to battery chemicals, arranged on said surfaces;

said second part and said partition wall forming a second space in said first part in which said electronics unit is disposed; and means for electrically connecting said battery unit in said first space and said electronics unit in said second space.

2. An active medical implant as claimed in claim 1 wherein said electrically insulating layer comprises at least one material selected from the group consisting of polyethylene, thermoplastic fluoropolymer film, fluorethene plastic, glass and cermet.

3. An active medical implant as claimed in claim 1 wherein said biocompatible material comprises titanium.

4. An active medical implant as claimed in claim 1 wherein said biocompatible material comprises stainless steel having an exterior coated with a material selected from the group consisting of perylene, tetrafluoroethylene and cermet.

5. An active medical implant as claimed in claim 1 wherein said means for electrically connecting said battery unit and said electronics unit comprises a plurality of electrical feedthroughs in said partition wall, said battery unit having two poles respectively connected through said feedthroughs to said electronics unit.

6. An encapsulated battery unit for an active medical implant, comprising a hermetically sealable capsule formed by a first bowl-shaped part closed by a second part, said first and second parts comprising biocompatible material and having an interior surface covered by an electrically insulating layer impermeable to battery chemicals.

7. An encapsulated battery unit as claimed in claim 6 wherein said electrically insulating layer comprises at least one material selected from the group consisting of polyethylene, thermoplastic fluoropolymer film, fluorethene plastic, glass and cermet.

8. An encapsulated battery unit as claimed in claim 6 wherein said biocompatible material comprises titanium.

9. An encapsulated battery unit as claimed in claim 6 wherein said biocompatible material comprises stainless steel having an exterior coated with a material selected from the group consisting of perylene, tetrafluorethylene and cermet.

10. An encapsulated battery unit as claimed in claim 6 wherein said insulating layer comprises an enclosure for said battery unit, said battery unit including two poles, and said encapsulated battery unit further comprising feedthroughs in said electrically insulating layer and in said second part for respectively receiving said poles of said battery unit.

* * * * *